United States Patent
Griffith et al.

(10) Patent No.: US 6,878,154 B2
(45) Date of Patent: Apr. 12, 2005

(54) TANNING DEVICE WITH PLANAR LAMPS

(75) Inventors: Roy L. Griffith, Indianapolis, IN (US); Randall J. Ballentine, Indianapolis, IN (US)

(73) Assignee: ETS, Inc., Indianapolis, IN (US)

( * ) Notice: Subject to any disclaimer, the term of this patent is extended or adjusted under 35 U.S.C. 154(b) by 123 days.

(21) Appl. No.: 10/391,681

(22) Filed: Mar. 19, 2003

(65) Prior Publication Data

US 2003/0187487 A1 Oct. 2, 2003

Related U.S. Application Data

(60) Provisional application No. 60/369,060, filed on Apr. 1, 2002.

(51) Int. Cl.[7] .............................. A61N 5/01; H01J 1/62
(52) U.S. Cl. .......................... 607/94; 607/91; 313/491; 313/493
(58) Field of Search .............................. 607/88, 90–91, 607/94; 313/491–493, 484, 634

(56) References Cited

U.S. PATENT DOCUMENTS

| | | | | |
|---|---|---|---|---|
| 4,499,403 A | * | 2/1985 | Leppelmeier et al. | ........ 313/487 |
| 5,319,282 A | * | 6/1994 | Winsor | ............ 315/169.4 |
| 6,075,320 A | * | 6/2000 | Winsor | .................. 315/94 |
| 6,461,376 B1 | * | 10/2002 | Beshore | ................ 607/91 |
| 6,639,351 B1 | * | 10/2003 | Tsai et al. | ............ 313/491 |
| 2002/0024294 A1 | | 2/2002 | Matsukawa et al. | ........ 313/493 |

OTHER PUBLICATIONS

"2002 Professional Catalog" of ETS, Inc.

* cited by examiner

*Primary Examiner*—Roy D. Gibson
(74) *Attorney, Agent, or Firm*—Woodard, Emhardt, Moriarty McNett & Henry LLP

(57) ABSTRACT

In certain embodiments, the present invention provides flat panel or planar lamps suitable to be placed in a body illuminating device and emitting fluorescent, ultraviolet radiation such that a person or user may be exposed to electromagnetic radiation suitable for tanning. In preferred embodiments, the invention includes a tanning device or system comprising at least one fluorescent, ultraviolet emitting planar lamp, and in certain embodiments the system uses an array of fluorescent, ultraviolet emitting planar lamps. In certain preferred embodiments, the lamp comprises at least one planar surface made of a material substantially transparent to ultraviolet radiation. A fluorescent or phosphor material is applied to the planar surface. An envelop is hermetically sealed over the planar surface to define a sealed volume containing the fluorescent material. A gas is dispersed within the volume, wherein the gas interacts with the fluorescent material when electrically excited to emit ultraviolet radiation.

17 Claims, 5 Drawing Sheets

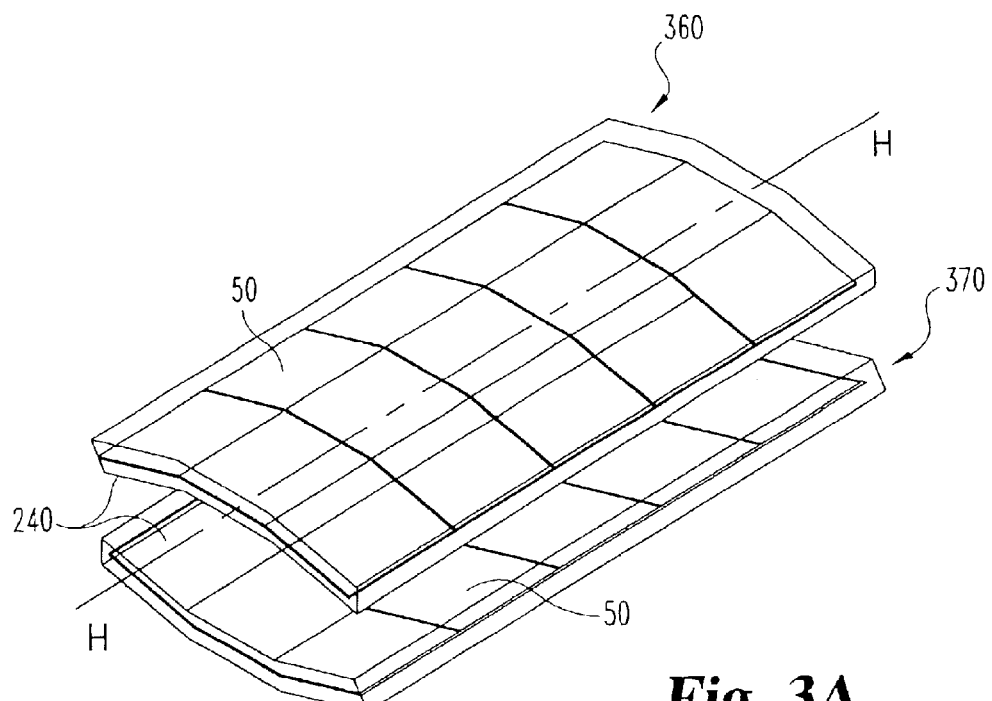
*Fig. 3A*
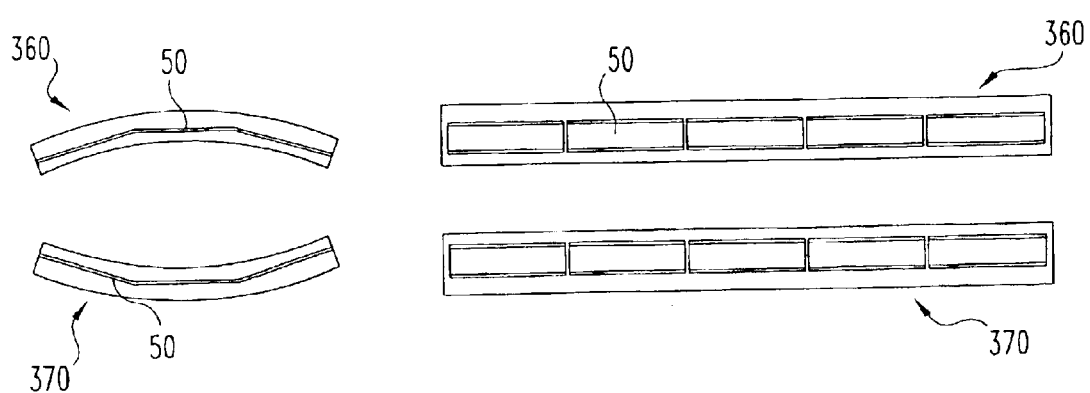
*Fig. 3C*  *Fig. 3B*

TANNING DEVICE WITH PLANAR LAMPS

This application claims priority to provisional application Serial No. 60/369,060 filed on Apr. 1, 2002, which is incorporated herein by reference.

FIELD OF THE INVENTION

This invention relates to an ultraviolet radiation emitting device or system for tanning the body. Examples of such devices include a tanning bed, tanning canopy, tanning booth, or face tanner. In particular, the invention relates to the manufacture and use of planar lamps for such devices.

BACKGROUND OF THE INVENTION

Many types of tanning bed or booth systems have two or more portions which are movable between an open position and a closed position for the ease of access of the user. Tanning lamps are mounted in these portions. When the portions are in the operating position, a volume or gap is defined between them where the person to be tanned or treated is oriented.

Traditional tanning beds or booths have used multiple tubular bulbs mounted in units in parallel horizontal or vertical arrays. Such bulbs require certain spacing tolerances for proper operation. Further, such bulbs create heat, and require a relatively high amount of power. Such bulbs can also be difficult or awkward to change. Typical tubular lamps, for example as used in tanning beds, require electrical connectors at opposing ends of the tubes. This requires electrical wiring and two sockets for each lamp, one at each end, adding to the cost and spacing requirements, limiting where such lamps can be mounted and requiring gaps between the bulbs.

In other fields, flat panel light emission devices have been used for, among other things, television and computer screens. However, flat panel lamps have not been designed to emit the wavelengths proper for use in tanning devices. In fact, such bulbs are specifically treated to prevent the emission of ultraviolet radiation.

The present invention relates to the modification of flat panel lamps to emit ultraviolet radiation suitable for tanning the body and types of apparatus having arrangements of such flat panel lamps. One advantage of such a system of lamps is that the emission of electromagnetic energy is more uniform than traditional tubular lamps. Additional preferred advantages are that the system is lighter and less bulky, is easier to maintain in temperature, reduces power requirements, and reduces the total number of lamps required for a comparably sized system.

A need exists for lighter, more efficient, and more effective tanning lamps and tanning apparatuses. The present invention satisfies these needs and provides other important advantages.

SUMMARY OF THE INVENTION

In certain embodiments, the present invention provides flat panel or planar lamps suitable to be placed in a body illuminating device and emitting fluorescent, ultraviolet radiation such that a person or user may be exposed to electromagnetic radiation suitable for tanning. In preferred embodiments, the invention includes a tanning device or system comprising at least one fluorescent, ultraviolet emitting planar lamp, and in certain embodiments an array of fluorescent, ultraviolet emitting planar lamps.

In certain preferred embodiments, the invention includes a fluorescent, ultraviolet emitting lamp for a tanning system. The lamp comprises at least one planar surface made of a material substantially transparent to ultraviolet radiation. A fluorescent or phosphor material is applied to the planar surface. An envelop is hermetically sealed over the planar surface to define a sealed chamber containing the fluorescent material. A gas is dispersed within the chamber, wherein the gas interacts with the fluorescent material when electrically excited to emit ultraviolet radiation.

It is an object of certain embodiments of the present invention to provide an improved lamp for use in ultraviolet illumination systems.

It is an object of certain other embodiments of the present invention to provide tanning systems and devices providing ultraviolet illumination to a user.

Further objects, features and advantages of the present invention shall become apparent from the detailed drawings and descriptions provided herein.

BRIEF DESCRIPTION OF THE DRAWINGS

FIGS. 3A–C include schematic views of arrays of flat panel lamps used in one embodiment of a horizontal "lay-down" tanning bed.

DESCRIPTION OF ILLUSTRATIVE EMBODIMENTS

Figure 1:
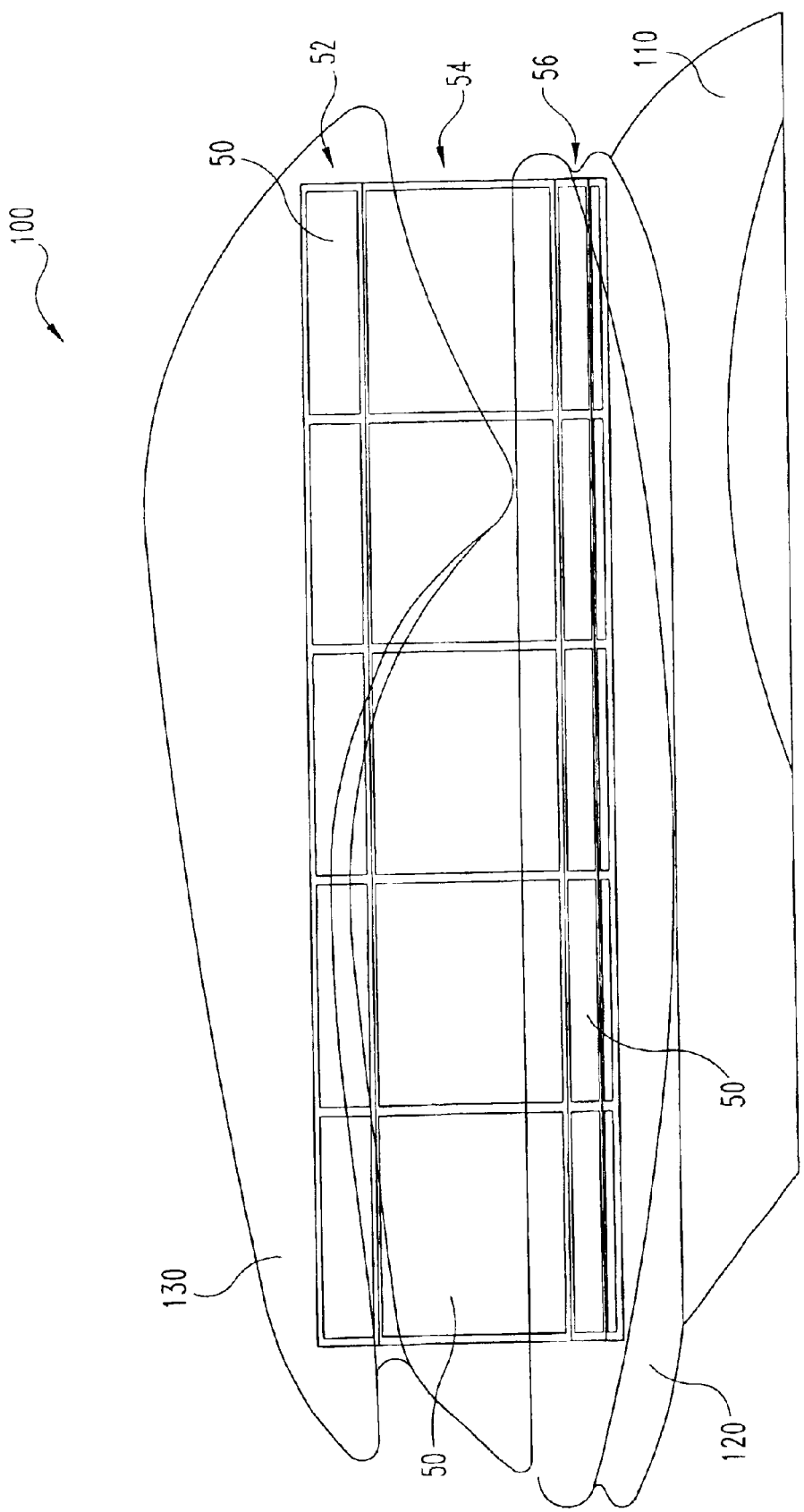
FIG. 1 is a partially transparent side view depiction of a tanning bed according to one preferred embodiment of the present invention.

For the purposes of promoting an understanding of the principles of the invention, reference will now be made to the embodiments illustrated and specific language will be used to describe the same. It will nevertheless be understood that no limitation of the scope of the invention is thereby intended, such alterations, modifications, and further applications of the principles of the invention being contemplated as would normally occur to one skilled in the art to which the invention relates.

Traditionally, ultraviolet illumination/radiation systems come in variety of configurations, including beds, booths, canopies and facial systems. These are often used by people to achieve the cosmetic affect of suntanned looking skin, or are often used for the medical benefits such as absorbing vitamin D. The present invention provides an improved lamp for use in such systems and provides an improved method of mounting lamps for more effective coverage of the person using the system. For explaining the present invention, a tanning bed and tanning booth are described in detail with references to a "person to be tanned;" however, it will be understood that this is not by way of limitation and various types of cosmetic and therapy systems and their users are being described. References herein to "ultraviolet illumination" are intended to mean the emission of radiation in the ultraviolet spectrum desired for tanning, and are not references to visible illumination, although visible illumination may be a by-product.

The present invention relates to the modification of flat panel lamps for tanning systems to emit ultraviolet radiation suitable for tanning the body. This includes in certain preferred embodiments various types of apparatus having arrangements of such flat panel lamps. Types of systems include beds, booths, canopies, and facial tanners, among others. One advantage of such a system of flat panel or planar lamps is that the emission of electromagnetic energy is more uniform than traditional tubular lamps. Additional preferred advantages are that the lamps and corresponding systems are lighter and less bulky, are easier to maintain in temperature, and use reduced power in comparison to traditional lamps. In certain arrangements, using planar lamps reduces the total number of lamps required for a comparably sized system.

One example of a non-ultraviolet planar lamp is manufactured by Osram. Modification of such prior planar lamps is required to enable them to emit radiation in the desired ultraviolet range. Modification may require removing or changing the internal phosphor, exchanging or altering the gas used inside the lamp, or using a filter in, attached to, or external to, the lamp to allow certain wavelengths to be emitted in the direction of the illuminated body. For the example of tanning the body, radiation emitted in the UVA or UVB range without radiation in the UVC range is desired.

To create planar lamps capable of emitting ultraviolet radiation suitable for tanning, a glass envelope is constructed using flat panels of glass. The glass is coated with phosphors and can be coated with a compound suitable for blocking wavelengths that are harmful to people, such as UVC radiation. Two panels of glass are connected by a glass seal or a frame such that there is a hermetically sealed space between the two panels. A gas suitable for emitting radiation when excited, such as xenon or mercury vapor, is placed in the sealed space between the two panels and a means of electrically exciting the gas is connected. Electrical connectors attach the lamp to a power supply. Preferably the electrical connectors used with lamps modified to emit ultraviolet radiation are substantially different from connectors used in non-modified lamps such that modified lamps cannot connect to non-modified lamp connectors and non-modified lamps cannot connect to modified lamp connectors. When connected to a power supply, the supplied energy results in the gas interacting with the phosphors on the glass and fluorescing, thereby creating radiation, as in standard fluorescent lights. Preferably a UV partial blocking compound in the planar lamp prevents unsuitable radiation from escaping the lamp. If an ultraviolet blocking coating is not used on the glass, an externally mountable filter may be used to prevent certain types of energy from reaching the tanning person.

FIG. 1 depicts a partially transparent side view example of a tanning bed 100. The tanning bed 100 consists of a base 110, to which is attached a bench 120 and a canopy 130. A plurality of planar lamps 50 are connected to the bench or the canopy either directly or indirectly through a framework or support structure. As illustrated, the bed includes an array of lamps 52 in canopy 130, an array 54 along a side and an array 56 in the base. The space between the bench 120 and canopy 130 is sufficient to allow a user to be comfortably placed. When using the system, a person lies on bench 120 in the space between base 110 and canopy 130. Ballasts and other accessories are well known, and are not shown for clarity. For purposes of this example, the side wall opposite the entry is considered part of the base and bench.

Figure 2:
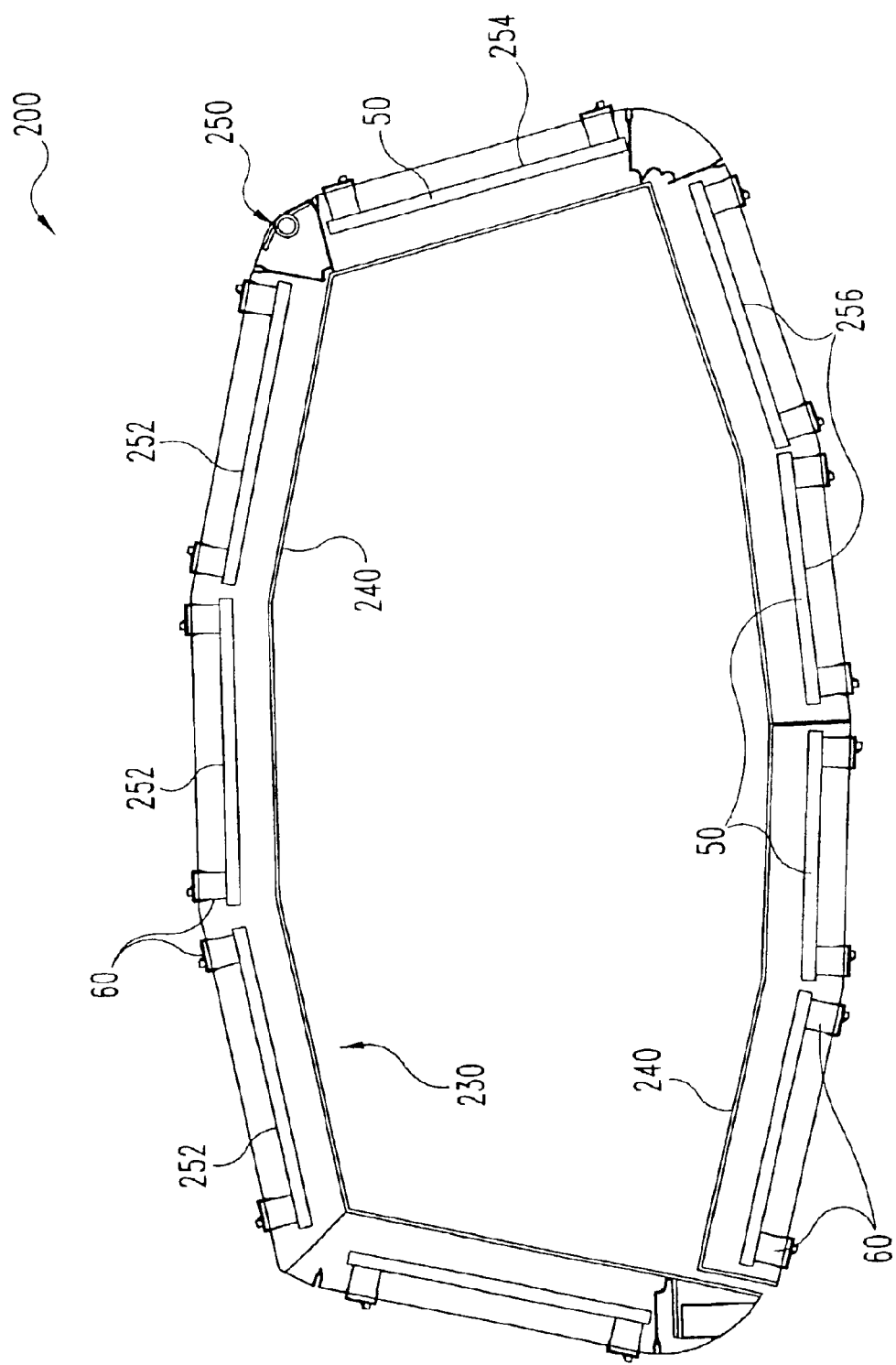
FIG. 2 is an end view depiction of a tanning bed.

FIG. 2 depicts an end view example of a tanning bed 200. Electrical connectors 60 attach the lamps 50 to the bench 220 or canopy 230 of the tanning bed 200. As illustrated, the bed 200 includes an array 252 in the canopy, an array 254 in the side and an array 256 in the base. Acrylic 240 is preferably placed between the planar lamps 50 and the tanning area to prevent the person tanning from contacting the lamps. In some embodiments the user lies upon the bench acrylic. This acrylic 240 may be designed to specifically filter certain types of light or to be generally transparent. A hinge 250 pivotally connects the canopy 230 to the bench 220, but may be differently positioned as required, to allow opening of the tanning bed 200 for easy entry and exit.

FIGS. 3A–C depict a schematic for an upper and lower array of lamps, 360 and 370, to provide uniform coverage in a tanning bed. For a conventional bed, the lamps 50 are arranged in substantially horizontal planes H, although the lamp planes may be slightly offset to correspond to contours or slightly "wrap-around" the typical user's body. The lamps 50 are preferably arranged such that there is minimal spacing between adjacent lamps in each array. Although the figure depicts similarly sized planar lamps, various combinations of different sized planar and non-planar lamps may be utilized. As one example, planar lamps can be used for facial tanning in conjunction with traditional tubular bulbs. The required number of lamps to accomplish coverage of a body will vary depending on individual lamp and system dimensions. In certain preferred embodiments, useful sizes for planar lamps generally range from approximately 4 to 24 inches on each side, and the useful shapes for the lamps include, but are not limited to, rectangles, triangles, and squares. By way of one example, the dimensions of the lamps depicted are approximately 15.3 inches by 12.9 inches. Acrylic 240 is used to prevent contact between the lamps 50 and the tanning person, but is not necessarily required.

FIGS. 4A–D depict a "stand-up" type tanning booth 400 having a lamp arrangement whereby each lamp 50 is attached to a support structure 410 that forms a cylindrical compartment comprised of a number of vertical columns 420 of lamps. For a booth, the lamps will be oriented in substantially vertical planes V. Although the figures depict similarly sized planar lamps, various combinations of different sized planar lamps and non-planar lamps may be utilized. The inside dimensions of the cylinder are sufficient to allow a person to comfortably stand. Depicted is an eight-sided cylinder with eight planar lamp columns 420 of five planar lamps 50 each. The total number of sides in the cylinder may differ from the eight sides depicted, and may, for example, include a front unit and a rear unit. Additionally, a planar lamp 50 is not required to be in alignment with the planar lamps below or above it such that the planar lamp columns 420 can be broken or skewed. As an optional feature, placed on top and/or the bottom of the cylinder are arrays of flat panel lamps 430 to emit ultraviolet light from above and/or below the user's body to tan the user's shoulders and/or the soles of their feet.

Figure 4D:
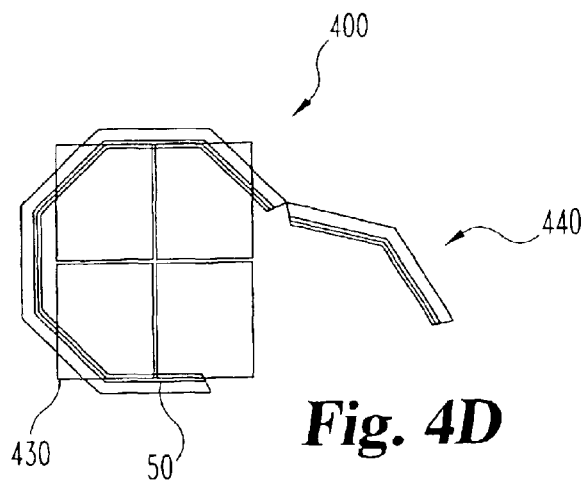
FIGS. 4A–D include schematic views of flat panel lamps used in one embodiment of a vertical "stand-up" tanning booth.
Figure 4C:
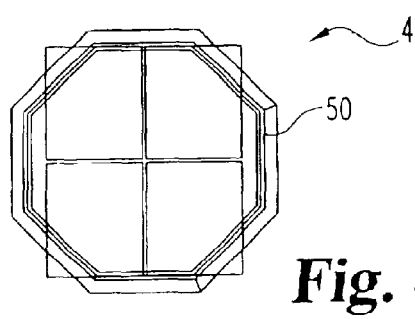
Figure 4B:
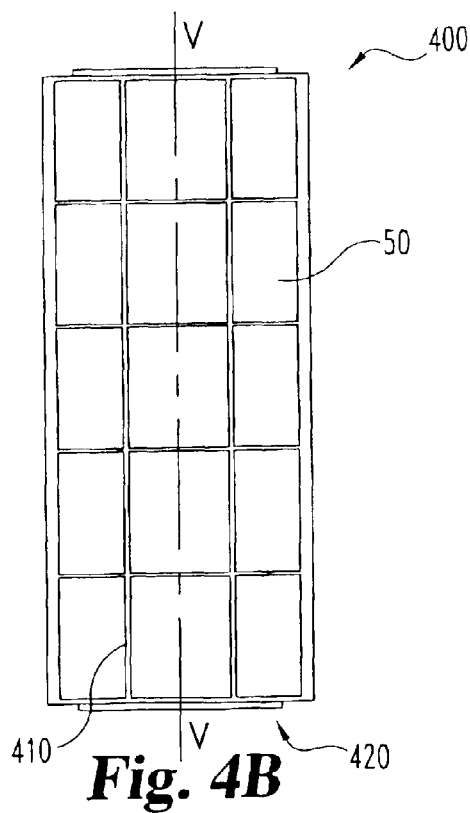
Figure 4A:
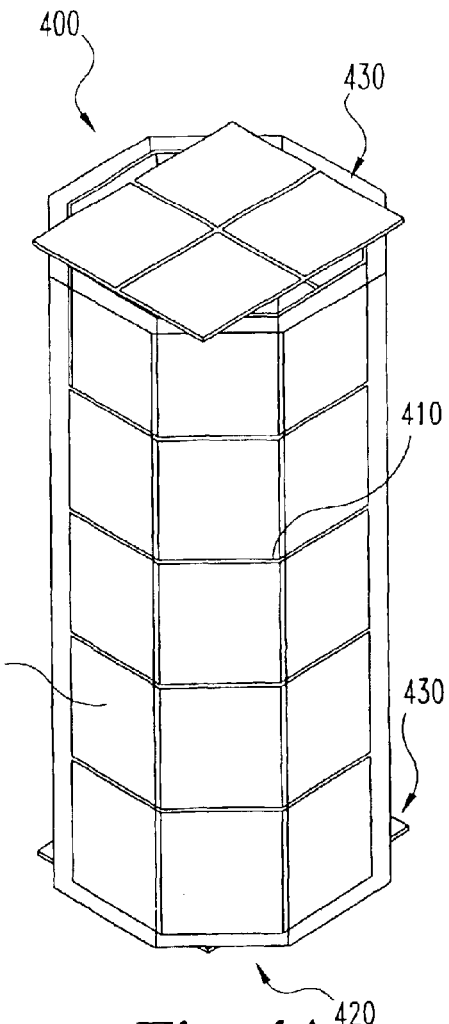

Various arrangements and various numbers of lamps may be used to achieve a similar result. The required number of lamps to accomplish coverage of a body will vary depending on individual lamp dimensions. Generally, one or more columns are hinged to form a door 440 such that the tanning booth 400 may be opened to allow easy entry and exit (FIG. 4D). In a preferred embodiment, a wire frame or grid or an acrylic panel(s) separate the tanning area from the lamps.

Figure 5A:
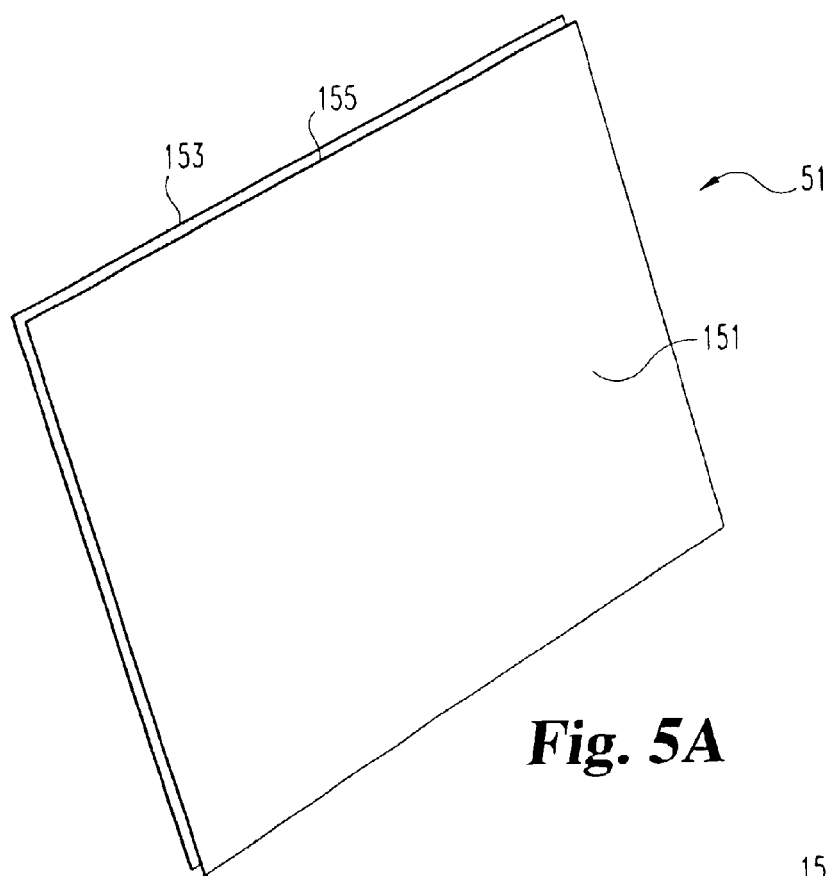
FIGS. 5A–C are an illustration of a flat panel lamp and power supply.
Figure 5B:
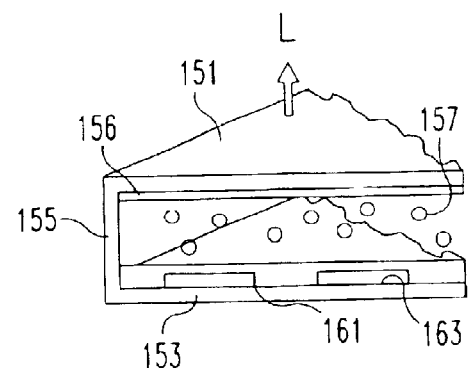
Figure 5C:
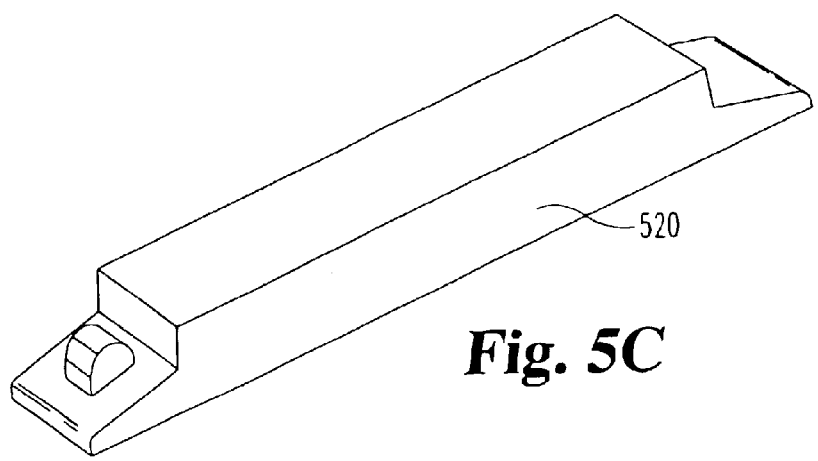

FIGS. 5A–C depict an ultraviolet planar lamp 51 and power converter 520. Lamp 51 preferably includes a first planar surface or panel 151 and a second planar surface or panel 153. Preferably, the second panel 153 is oriented in a plane parallel to first panel 151. First panel 151 is sealed to second panel 153 to form an envelope between them, with side walls 155. Sidewalls 155 may be formed integrally with the panels, such as a glass envelope, or the panels may be separately sealed using methods such as caulk, glue, a rubber gasket or a sealed molding. Preferably a fluorescent layer or phosphors 156 is applied to at least first panel 151. An appropriate excitable gas 157 (such as xenon or mercury) is dispersed as a vapor in the envelope volume between first panel 151 and second panel 153.

Lamp 51 further includes a cathode electrode 161 and an anode electrode 163, covered by an isolation layer 165. Cathode 161 and anode 163 are operably connected to power converter 520. Lamp 51 is operated by applying electricity to cathode 161 and anode 163 to excite gas 157. When electrically excited, the gas 157 interacts with the fluorescent or phosphor layer 156 to emit ultraviolet light L towards the system user. Optionally, the second panel 153 may also be coated with a phosphor to emit additional light, which may be reflected internally or externally towards the system user. Visible light may be a by-product of the lamp.

As a way of illustration, example specifications for a lamp 51, based on the specifications for a non-ultraviolet lamp made by Osram, include a supply voltage of 24 volts DC creating an output luminance of 5,000 $cd/m^2$, with luminance after 1 BEF of 7,500 $cd/m^2$. The lamp power/area is approximately 0.065 $W/cm^2$. The Lamp power may be 48 Watts with dimensions of 324 mm×258 mm×10 mm (12.8 in.×10.2 in×0.39 in).

Mounting of the lamps to the tanning apparatus may be accomplished in different ways. The preferred method is to have a frame with mounting holes for the lamps and wiring harnesses with connectors attached such that the lamps may be connected to a power supply (not shown). Generally, the wiring will be internal to the tanning system along with the converters necessary to convert local community outlet power, typically 110 or 220 VAC, to the power required for the lamps. Preferably, for ultraviolet lamps, the connectors and/or the power converter 520 are incompatible with non-ultraviolet light emitting lamps and/or power converters.

In certain embodiments, reflectors may be mounted behind the lamps to redirect ultraviolet radiation emitted in a direction away from the tanning area back towards the tanning area. As a preferred feature of the present invention, planar lamps of the present invention are mounted more closely together than traditional tubular bulbs can be mounted. This minimizes the space between the bulbs and the resultant need for reflectors. In a still further embodiment, the rear glass panel of the lamp's glass envelope may include a reflector, which internally redirects ultraviolet radiation out the preferred face of the lamp.

As a further advantage, planar lamps can be packaged, shipped and stored in compact cartons, saving in shipping and storage costs over elongate bulbs which frequently have awkward lengths and require special handling.

While the invention is shown in the preferred context of a tanning bed or tanning booth, the concepts also encompass tanning canopies, face tanners, and other devices which emit tanning light, as well as light emitting devices without significant ultraviolet light such as may be used to lower bilirubin levels in infants, or to treat seasonal affective disorder in adults.

Additionally, while the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A tanning device comprising at least one fluorescent, ultraviolet externally emitting planar lamp, wherein said tanning device is selected from the group consisting of a tanning bed, a tanning booth, a tanning canopy and a facial tanner.

2. A tanning system, comprising an array of fluorescent, ultraviolet emitting planar lamps.

3. The tanning system of claim 2, wherein said system comprises a bed.

4. The tanning system of claim 2, wherein said system comprises a booth.

5. The tanning system of claim 2, wherein said system comprises a canopy.

6. A tanning system, comprising:

a) a first unit;

b) a second unit mounted to be positioned in an operating position with respect to said first unit such that said first and second units define a gap for a person to be tanned to be oriented; and, c) an array of fluorescent, ultraviolet emitting planar lamps mounted to said first and second units.

7. The tanning system of claim 6, wherein said planar lamps are mounted in substantially vertical planes.

8. The tanning system of claim 6, wherein said lamps are mounted in substantially horizontal planes.

9. A fluorescent, ultraviolet emitting lamp and a tanning device, comprising:

a) at least one planar surface made of a material substantially transparent to ultraviolet radiation in wavelengths suitable for tanning a person;

b) a fluorescing material applied to said surface;

c) an envelop hermetically sealed over said planar surface to define a sealed volume over said fluorescent material; and, d) a gas dispersed within said volume, wherein said gas interacts with said fluorescent material when electrically excited to emit ultraviolet radiation;

e) wherein the lamp is mounted in a tanning device selected from the group consisting of a tanning bed, a tanning booth, a tanning canopy and a facial tanner.

10. The lamp of claim 9, wherein said envelop further comprises a second planar surface made of a material substantially transparent to said planar surface.

11. The lamp of claim 10, wherein said second planar surface is coated with a fluorescing material.

12. The lamp of claim 10, wherein said second planar surface reflects ultraviolet radiation internally towards said at least one planar surface.

13. The lamp of claim 10, wherein said second planar surface is mounted in said envelop substantially parallel to said first planar surface.

14. The lamp of claim 13, wherein said planar surfaces are made of glass.

15. The lamp of claim 14, wherein said glass is treated to be substantially opaque to UVC radiation.

16. The lamp of claim 9, further comprising a filter mountable adjacent said planar surface which is substanially opaque to UVC radiation.

17. The lamp of claim 9, further comprising at least two electrodes through which electricity can be applied to said gas.

* * * * *